(12) United States Patent
Trueeb et al.

(10) Patent No.: US 8,400,306 B2
(45) Date of Patent: Mar. 19, 2013

(54) LABORATORY DEVICE, LABORATORY RACK ASSEMBLY AND METHOD FOR COUPLING AN RFID CHIP

(75) Inventors: Heinz Trueeb, Hochdorf (CH); Armin Birrer, Steinhausen (CH); Thomas Brauner, Zurich (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 436 days.

(21) Appl. No.: 12/356,361

(22) Filed: Jan. 20, 2009

(65) Prior Publication Data

US 2011/0095864 A1 Apr. 28, 2011

(30) Foreign Application Priority Data

Jan. 18, 2008 (EP) .................................. 08000933

(51) Int. Cl.
*G08B 13/14* (2006.01)
(52) U.S. Cl. ............... 340/572.7; 340/568.1; 340/572.1; 340/10.1
(58) Field of Classification Search ............... 340/572.7, 340/568.1, 571, 539.1, 572.1, 10.1, 10.2, 340/10.31, 10.32, 5.91; 705/22, 23, 28; 343/702, 343/876, 878, 893
See application file for complete search history.

(56) References Cited

U.S. PATENT DOCUMENTS

| | | | | |
|---|---|---|---|---|
| 5,285,907 A | * | 2/1994 | Franchere et al. | 211/74 |
| 5,537,126 A | * | 7/1996 | Kayser et al. | 345/2.1 |
| 5,936,527 A | * | 8/1999 | Isaacman et al. | 340/572.1 |
| 6,122,492 A | * | 9/2000 | Sears | 455/127.1 |
| 6,392,544 B1 | * | 5/2002 | Collins et al. | 340/572.7 |
| 2003/0132835 A1 | | 7/2003 | Lin et al. | |

FOREIGN PATENT DOCUMENTS

| | | |
|---|---|---|
| DE | 19528445 A1 | 2/1996 |
| DE | 102005028441 A1 | 12/2006 |
| EP | 1130377 B1 | 9/2004 |
| EP | 1785913 A2 | 5/2007 |
| EP | 1870834 | 12/2007 |
| EP | 08000933 | 6/2008 |
| WO | 0227682 A | 4/2002 |

\* cited by examiner

*Primary Examiner* — Anh V La
(74) *Attorney, Agent, or Firm* — M. Reza Savari; Olga Kay

(57) ABSTRACT

Devices and methods for the identification of test tubes in a test tube rack having a RFID chip, and including an antenna structure elements for wireless coupling with the RFID chip, such that the location of the RFID chip determines the orientation of the test tube rack and the position of the test tube, and coupling of the RFID chips attached to the test tube racks is independent of the direction of insertion of the test tube rack.

17 Claims, 1 Drawing Sheet

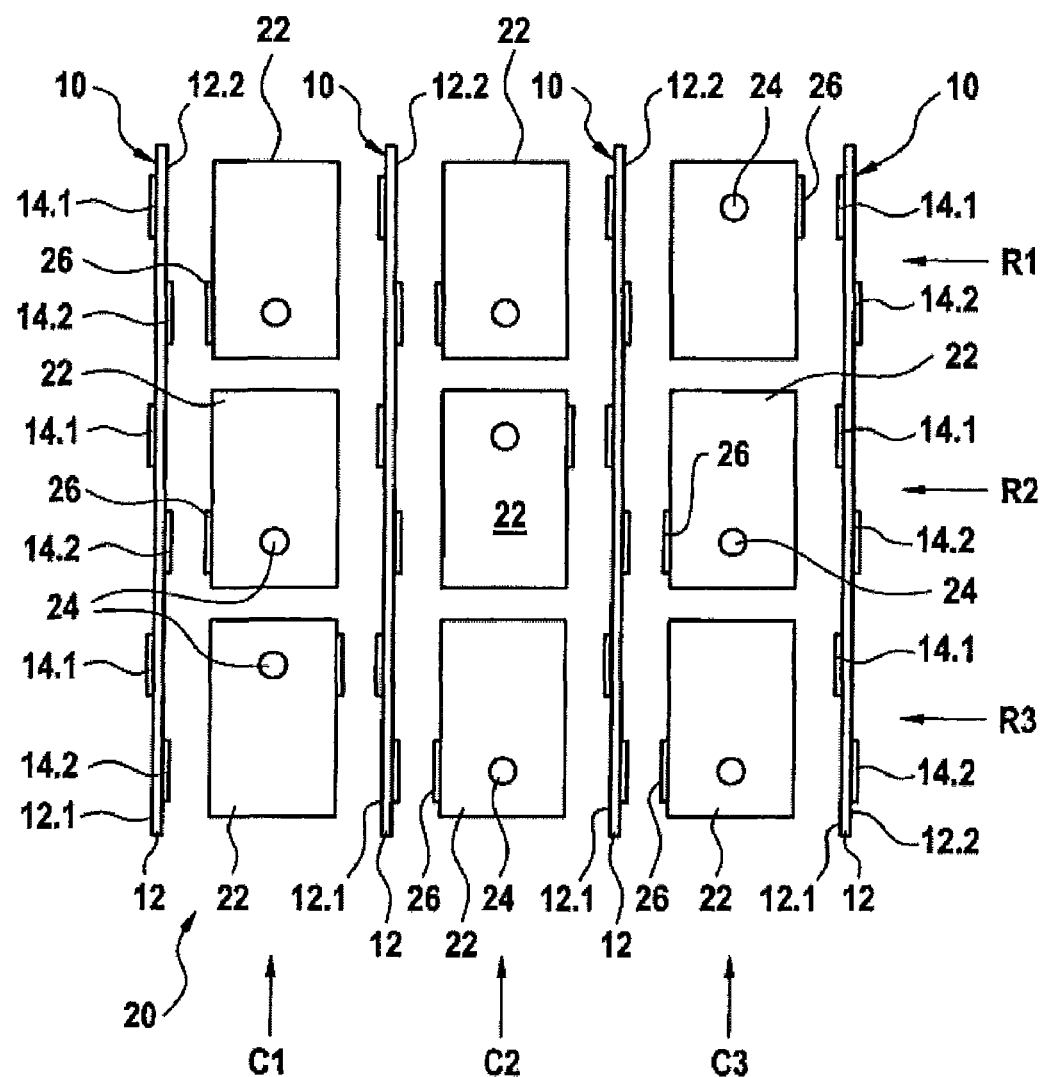

LABORATORY DEVICE, LABORATORY RACK ASSEMBLY AND METHOD FOR COUPLING AN RFID CHIP

CROSS-REFERENCES TO RELATED APPLICATION

The present application claims the benefit of EP Appl. No. 08 000 933.5 filed Jan. 18, 2008, the entire content of which is hereby incorporated herein by reference in entirety.

FIELD OF THE INVENTION

The present invention relates to the identification of laboratory vessels in a laboratory rack using RFID technology.

DESCRIPTION OF PRIOR ART

Laboratory devices are important work tools and systems in laboratory analytics in the clinical area, chemical and pharmaceutical area, in immunology etc. Modern laboratory or analyser devices are conceived in a modular manner and provide for fully automated laboratory work. Different modules relate to different fields of analytics, using for example dispenser technology or pipette technology. Reagents and specimens used in the analytical work are usually provided in laboratory vessels, i.e. individual containers such as test tubes or reagent containers, wherein one or more containers are placed in a container carrier structure. Container carrier structures are well-known in this field of technology under various terms such as racks, cassettes, cartridges etc. For ease of reference, all these holding devices will be referred to as laboratory racks or just racks throughout this application. Further, the terms laboratory vessel or reagent container will be used as synonym for any kind of suitable container.

In the course of the analysing process, one or more laboratory racks holding each at least one laboratory vessel are placed in a respective analyser device. In order for the analyser device to be able to treat the inserted carrier structure properly, i.e. identifying its content etc., each laboratory vessel usually comprises a barcode label on its outer surface. The analyser device in turn comprises a barcode reader installed in such a manner that the barcode information contained on the label of the laboratory vessel can be read and transferred to a computing and control unit of the analyser device.

With the advent of RFID technology in laboratory work, particularly for identification of reagent work probes, RFID assemblies on laboratory vessels and other reagent containers have become more and more widespread.

Radio Frequency Identification (RFID) provides a convenient mechanism for identifying and detecting objects using wireless electromagnetic signals. A basic RFID system has at least one RFID reader and at least one RFID assembly (the latter also known by the term "transponder" or "RFID tag"). Typically, RFID readers may include a coil or antenna and circuitry to transmit and receive signals with the coil or antenna. An RFID assembly or tag or transponder also may include a coil or antenna and information stored on an RFID chip that can be read by an RFID reader.

The RFID reader antenna generates an electromagnetic field, thereby transferring energy to the tag. Depending on the design of the tag, a portion of the energy transferred to the tag will be reflected to the reader so as to provide information about the tag back to the reader. Some RFID systems can be used to read and optionally write data to and from the RFID tag. RFID readers can generate signals spanning distances from less than one centimetre to more than fifty metres depending on frequency and power of the signals generated at the RFID reader antenna.

Typically, RFID assemblies or tags are categorised as either active or passive. Active RFID tags are powered by an internal battery and are typically read/write, i.e. tag data can be rewritten and/or modified. An active tag's memory size varies according to application requirements, some systems operating with up to 1 MB of memory and more. Passive RFID tags operate without a separate external power source and obtain operating power generated from the reader. Passive tags are consequently typically lighter than active tags, less expensive, and offer a long operational lifetime. Passive tags typically have shorter read ranges than active tags and require a higher-powered reader. Read-only tags are typically passive and can be programmed with a unique set of data (usually 32 to 128 bits) that is typically predetermined at the time of manufacture of the tag. It is understood that passive read/write tags can also be employed consistent with the present teachings.

EP 1 130 377 B1 discloses racks with specimen slides inserted therein, the racks each comprising a transponder. Several of the racks are connected in series. The racks with the specimen slides therein traverse individual processing stations, and the transponders of the racks can be read out by means of excitation coils which are assigned to the processing stations. The racks can be identified within short time intervals with the aid of the transponders attached thereto and can be assigned to a specific processing procedure. Each rack to be identified is assigned its own excitation coil with respective complete electronic evaluation unit.

SUMMARY OF THE INVENTION

In one aspect, the invention relates to a laboratory device comprising a rack holding assembly for holding laboratory racks, an antenna structure element for wireless coupling with an RFID chip of a laboratory rack, the antenna structure element comprising a substantially flat carrier substrate with a first carrier surface and a second carrier surface opposite the first carrier surface, and comprising at least two antennas applied on the carrier substrate, wherein a first antenna of the at least two antennas is applied on the first carrier surface and a second antenna of the at least two antennas is applied on the second carrier surface.

In another aspect, the invention relates to a rack assembly for holding a plurality of laboratory racks, comprising a plurality of rack receptacles for receiving and holding the laboratory racks in a row-and-column structure, and further comprising a plurality of antenna structure elements for wireless coupling with an RFID chip of a laboratory rack, wherein the antenna structure elements are arranged parallel to each other between columns or rows of rack receptacles in such a manner that coupling of RFID chips attached to the racks is possible independently of the direction of insertion of the respective rack.

In yet another aspect, the invention relates to a method to for couple coupling an RFID chip of a laboratory rack, comprising the following steps of providing at least two antenna element structures according to the invention; placing the antenna element structures in parallel to each other so that their respective carrier surfaces are facing the carrier surfaces of each adjacent antenna element structure; placing one or more laboratory racks with RFID chips on each respective laboratory rack between two adjacent antenna element structures; and consecutively or simultaneously energising each antenna.

In a further aspect, the invention relates to a laboratory device according to the invention, wherein the laboratory device comprises at least one of an element selected from the group consisting of a pipetting device, a stirrer, a tempering device, a shaker, and an agitator.

In still another aspect, the invention relates to an antenna structure element for wireless coupling with an RFID chip of a test tube rack, the antenna structure element comprising a substantially flat carrier substrate with a first carrier surface and a second carrier surface opposite the first carrier surface, and comprising at least two antennas applied on the carrier substrate, wherein a first antenna of the at least two antennas is applied on the first carrier surface and a second antenna of the at least two antennas is applied on the second carrier surface.

In yet another aspect, the invention relates to a rack assembly for holding a plurality of laboratory racks, comprising a plurality of rack receptacles for receiving and holding the laboratory racks in a row-and-column structure, and further comprising a plurality of antenna structure elements for wireless coupling with an RFID chip of a laboratory rack, wherein each antenna structure element comprises a substantially flat carrier substrate with a first carrier surface and a second carrier surface opposite the first carrier surface, and comprising at least two antennas applied on the carrier substrate, wherein a first antenna of the at least two antennas is applied on the first carrier surface and a second antenna of the at least two antennas is applied on the second carrier surface, the two antennas being applied on the two carrier surfaces in a staggered format such that the offset between the two antennas corresponds to two possible locations of the RFID laboratory rack chip to be read in the rack assembly.

BRIEF DESCRIPTION OF THE FIGURE

FIG. 1 shows a top view of an embodiment of a rack assembly comprising several antenna structure elements according to the invention.

DETAILED DESCRIPTION OF THE INVENTION

The present invention relates to the identification of the orientation of a laboratory rack, and an antenna structure element for wireless coupling with an RFID chip.

According to an embodiment of the invention, a laboratory device for the processing of reagents, samples, specimens and the like comprises a rack holding assembly for holding a plurality of laboratory racks as well as an antenna structure element for wireless coupling with an RFID chip of the laboratory rack. The antenna structure element comprises a substantially flat carrier substrate with a first carrier surface and a second carrier surface opposite the first carrier surface. The antenna structure element further comprises at least two antennas applied on the carrier substrate, wherein a first antenna of the at least two antennas is applied on the first carrier surface and a second antenna of the at least two antennas is applied on the second carrier surface.

Thus, the laboratory device with an antenna structure element according to the invention allows precise localisation of objects bearing RFID chips or tags on either side of the antenna structure element. It also facilitates setting up of laboratory rack assemblies as the antenna assembly in such a rack assembly can be easily set up by arranging a desired number of antenna structure elements parallel to each other in such a manner that laboratory racks can be placed in between two adjacent parallel antenna structure elements, as described in more detail below.

Thus, one further aspect of the invention relates to a rack assembly for holding a plurality of laboratory racks, the rack assembly comprising a plurality of rack receptacles for receiving and holding the laboratory racks in a row-and-column structure, and further comprising a plurality of antenna structure elements, according to the invention, wherein the antenna structure elements are placed parallel to each other between columns or rows of rack receptacles in such a manner that coupling of RFID chips attached to the racks is possible independently of the direction of insertion of the respective rack.

According to one possible embodiment, the two antennas are applied on the two carrier surfaces in a staggered format, i.e. the second antenna on the second carrier surface is offset as to the location of the first antenna on the first carrier surface on the other side of the carrier substrate. There is a possibility of arranging the two antennas in such a manner that the offset corresponds to two possible locations of the RFID chip to be read in the rack assembly, with the result that independent of the orientation of the laboratory rack the RFID chip of the rack is always located in the vicinity to either one of the antennas.

There are a number of possible ways to apply the antennas to the carrier. This includes printing, depositing, by lithographic techniques or by means of adhesion or other methods well known to the person skilled in the art. Possible materials for realizing the antennas, e.g. by printing, are copper or aluminium. However, any other electrically conducting material is suitable. The antenna structure element of the invention can, for example, be implemented as a printed circuit board with the antennas printed thereon.

A still further aspect of the invention relates to a method to couple an RFID chip of a laboratory rack, said method comprising providing at least two antenna element structures according to the invention and placing these antenna element structures in parallel to each other so that their respective carrier surfaces are facing the carrier surfaces of each adjacent antenna element structure. The method further comprises placing one or more laboratory racks with RFID chips on each respective laboratory rack between two adjacent antenna element structures and consecutively or simultaneously energising each antenna.

Further features and embodiments will become apparent from the description and FIG. 1.

It will be understood that the features mentioned above and those described hereinafter can be used not only in the combination specified but also in other combinations or on their own, without departing from the scope of the present disclosure.

Various implementations are schematically illustrated in FIG. 1 by means of an embodiment by way of example and are hereinafter explained in detail with reference to FIG. 1. It is understood that the description is in no way limiting on the scope of the present disclosure and is merely an illustration of a preferred embodiment.

Wherever possible, the same reference numbers are used throughout FIG. 1 to refer to the same or like parts.

The terms "RFID assembly" and "RFID tag" as used herein refers to either an active or passive RFID tag that contains information. The RFID tag may be read-only or read/write. The information associated with the RFID tag may be hard-coded into the RFID tag at the time of manufacture or at some later time or the RFID tag may contain information that is written to the RFID tag throughout its lifetime.

The term "RFID reader" as used herein includes devices that can read information from and/or write information into an RFID tag.

The term "information" as used herein refers to data that can be stored electronically in the RFID tag and can be retrieved to be used as machine readable or human readable data for processing the reagent or specimen and/or laboratory vessel and/or laboratory rack and/or can be written to the RFID tag during or after processing. It covers but is not restricted to information such as type of reagent, specimen, lot size, donor, production or donation date, production or donation place, application data, system type suitability, use-by date, set point, control point, calibration data, analyser device log data, date of first opening, used in which device, sampling data, carrier structure control data, and the like.

The term "laboratory vessel" as used herein refers to any kind of container which is suitable for accommodating any kind of reagent, specimen or substance to be used in the context of clinical and/or biological and/or pharmaceutical laboratory diagnostics and/or analysis. Such containers can be, but are not limited to, tube-shaped containers of circular or square cross-section. Also covered are containers with one or several chambers/cells for receiving different liquids.

The term "laboratory device" as used herein refers to any kind of automated or semi-automated system for use in laboratory work in the clinical, chemical, biological, immunology or pharmaceutical area or the like. Such a laboratory device may comprise, amongst, others, at least one of a pipetting device, a stirrer, a tempering device, a shaker, or an agitator.

FIG. 1 shows in schematic manner a top view of an embodiment of a laboratory rack assembly 20 according to the invention.

The rack assembly 20 comprises a variety of antenna structure elements 10 according to the invention. In the illustration of FIG. 1, four antenna structure elements 10 are shown. Each antenna structure element 10 comprises a carrier substrate 12. In the illustrated embodiment, the carrier substrate 12 is substantially flat and elongated and has a first carrier surface 12.1 and a second carrier surface 12.2, the latter being opposite to the first carrier surface 12.1. Further, each antenna structure element comprises a plurality of antennas 14 which are shown in schematic manner in the illustration of FIG. 1. The antennas may be of any conventional form, e.g. dipoles, coils, and the like.

According to an embodiment of the invention, the antennas 14 are applied on both carrier surfaces 12.1, 12.2 in an alternating manner along the longitudinal direction of the carrier substrate 12 (which in the illustration of FIG. 1 is from top to bottom or in the direction of arrows C1, C2 and C3). Thus, a first antenna 14.1 is applied on the first carrier surface 12.1 of each antenna structure element and a second antenna 14.2 is applied on the second carrier surface 12.2 opposite the first carrier surface 12.1, and so on for following pairs of first and second antennas 14.1, 14.2, so that each antenna structure element 10 comprises a plurality of antennas which are distributed on both sides of the carrier substrate 12 alternatingly in a staggered format. The term "staggered format" describes the fact that the antennas are applied on the opposite sides of the carrier substrate with an offset to each other, which will be explained in more detail below.

In the spaces between the parallel antenna structure elements 10, laboratory racks 22 can be placed into rack receptacles (not shown) in a row-and-column structure as can be seen from FIG. 1. In the embodiment shown in FIG. 1, a total of nine laboratory racks 22 are placed between the four antenna structure elements 10 to form a matrix structure of three columns C1, C2, C3 and three rows R1, R2 and R3. However, it will be appreciated that any number of racks in numerous arrangements may be used.

Each laboratory rack 22 comprises an RFID chip 26 applied thereon. The RFID chip or tag 26 is applied on one side surface of the rack 22, which rack has a generally rectangular shape.

Further, each rack 22 holds at least one test tube 24 (in the illustration of FIG. 1, each rack 22 comprises only one reagent container 24 for illustrative purposes; however, each rack 22 can comprise more than just one reagent container). For illustrative purposes, only the reagent container 24 containing a substance to be pipetted is shown in the illustration of FIG. 1. The RFID chip 26 is applied on the side surface of the rack 22 in a position offset as to the centre axis of the rack 22, i.e. the location of the RFID chip 26 allows to deduce an orientation of the rack 22 and thus the position of the reagent container 24.

Due to the design of the antenna structure elements 10 of the invention with the antennas 14.1, 14.2 positioned in a staggered format, offset one to each other by a distance corresponding to the respective position of the RFID chip of the rack 22 in its respective two positions depending on the direction in which the rack 22 has been inserted in the rack assembly 20, the invention allows to easy determination of the orientation of a particular rack.

In order to obtain precise measurements, the RFID antennas 14.1, 14.2 may be designed in such a manner to have a short range of transmission, i.e. the range of the antennas may be limited in such a manner that only the antenna positioned next to the RFID chip 26 can actually couple with this RFID chip and read it.

Energising of the antennas may be performed either in a consecutive manner or simultaneously. In one possible embodiment, the antennas may be operated in multiplex operation as part of a multiplexer circuitry, in which case a reading of the labels would be performed sequentially or consecutively. Due to the limitation of the range of each individual antenna, a precise localization of the read chip and thus determination of the position of the corresponding reagent container is possible.

As can be easily seen from the illustration in FIG. 1, if any one of the racks 22 is taken out of the rack assembly 20, turned about 180° and put back into the rack assembly 20, the RFID chip 26 can still be read by the antenna applied on the antenna structure element on the opposite side of the column. As a result of the correct determination of the orientation of the rack, any operation to be performed with the reagent container, e.g. pipetting, can be properly controlled, and the user of the system can insert the racks into the rack assembly without the need to observe the orientation during inserting.

Although certain embodiments of the invention have been described using specific terms, such description is for illustrative purposes only, and it is to be understood that changes and variations may be made without departing from the spirit or scope of the following claims.

While the foregoing invention has been described in some detail for purposes of clarity and understanding, it will be clear to one skilled in the art from a reading of this disclosure that various changes in form and detail can be made without departing from the true scope of the invention. For example, the devices, assemblies and methods described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A laboratory device comprising:
a rack holding assembly,
one or more laboratory racks for holding at least one laboratory vessel, the one or more laboratory racks having a generally rectangular shape with a RFID chip applied to one side surface in a position offset as to the center axis of the laboratory rack, such that the location of the RFID chip determines the orientation of the laboratory rack and the position of the at least one laboratory vessel, and
an antenna structure element for wireless coupling with the RFID chip of the one or more laboratory rack, the antenna structure element comprising a substantially flat carrier substrate with a first carrier surface and a second carrier surface opposite the first carrier surface, and comprising at least two antennas applied on the carrier substrate, wherein a first antenna of the at least two antennas is applied on the first carrier surface and a second antenna of the at least two antennas is applied on the second carrier surface, the at least two antennas positioned in a staggered manner on alternating locations on the first and second carrier surfaces offset to each other by a distance corresponding to the position of the RFID chip of the laboratory rack, wherein coupling of the RFID chips attached to the laboratory racks is independent of the direction of insertion of the laboratory rack.

2. The laboratory device according to claim 1, further comprising a plurality of rack receptacles capable of holding the laboratory racks in a row-and-column structure.

3. The laboratory device according to claim 2, wherein the antenna structure elements are arranged parallel to each other between columns or rows of rack receptacles.

4. The laboratory device according to claim 1, wherein the at least two antennas are printed on the carrier substrate.

5. The laboratory device according to claim 1, wherein the at least two antennas are deposited on the carrier substrate.

6. The laboratory device according to claim 1, wherein the at least two antennas are adhered onto the carrier substrate.

7. The laboratory device according to claim 1, wherein the at least two antennas are made of copper or aluminum.

8. The laboratory device according to claim 1, wherein the at least two antennas are produced by a (photo-)lithography process.

9. The laboratory device according to claim 1, wherein the carrier substrate is a substantially flat elongated substrate comprising an even number of antennas distributed on both carrier surfaces.

10. The laboratory device according to claim 9, wherein the antennas are applied alternatingly on the two carrier surfaces along the longitudinal direction of the carrier substrate.

11. The laboratory device according to claim 1, wherein the antennas have a short range of transmission.

12. A method for coupling an RFID chip of a laboratory rack, comprising:
providing at least two antenna element structures according to claim 1;
placing the antenna element structures in parallel to each other so that their respective carrier surfaces are facing the carrier surfaces of each adjacent antenna element structure;
placing one or more laboratory racks with RFID chips on each respective laboratory rack between two adjacent antenna element structures; and
consecutively energising each antenna.

13. A method for coupling an RFID chip of a laboratory rack, comprising:
providing at least two antenna element structures according to claim 1;
placing the antenna element structures in parallel to each other so that their respective carrier surfaces are facing the carrier surfaces of each adjacent antenna element structure;
placing one or more laboratory racks with RFID chips on each respective laboratory rack between two adjacent antenna element structures; and
simultaneously energising each antenna.

14. A laboratory device according to claim 1, wherein the laboratory device comprises at least one of member selected from the group consisting of a pipetting device, a stirrer, a tempering device, a shaker, and an agitator.

15. A rack assembly for holding a plurality of laboratory racks comprising:
a plurality of rack receptacles for receiving and holding the laboratory racks in a row-and-column structure, the laboratory racks having a generally rectangular shape with a RFID chip applied to one side surface in a position offset as to the center axis of the laboratory rack, such that the location of the RFID chip determines the orientation of the laboratory rack, and
a plurality of antenna structure elements for wireless coupling with the RFID chip of the laboratory rack, the antenna structure element comprising a substantially flat carrier substrate with a first carrier surface and a second carrier surface opposite the first carrier surface, and comprising at least two antennas applied on the carrier substrate, wherein a first antenna of the at least two antennas is applied on the first carrier surface and a second antenna of the at least two antennas is applied on the second carrier surface, the at least two antennas positioned in a staggered manner on alternating locations on the first and second carrier surfaces offset to each other by a distance corresponding to the position of the RFID chip of the laboratory rack, wherein coupling of the RFID chips attached to the laboratory racks is independent of the direction of insertion of the laboratory rack, wherein the antenna structure elements are arranged parallel to each other between columns or rows of rack receptacles.

16. An antenna structure element for wireless coupling with an RFID chip of a test tube rack for holding at least one test tube, the test tube rack having a generally rectangular shape with a RFID chip applied to one side surface in a position offset as to the center axis of the test tube rack, such that the location of the RFID chip determines the orientation of the test tube rack and the position of the at least one test tube, the antenna structure element comprising a substantially flat carrier substrate with a first carrier surface and a second carrier surface opposite the first carrier surface, and comprising at least two antennas applied on the carrier substrate, wherein a first antenna of the at least two antennas is applied on the first carrier surface and a second antenna of the at least two antennas is applied on the second carrier surface, the at least two antennas positioned in a staggered manner on alternating locations on the first and second carrier surfaces offset to each other by a distance corresponding to the position of the RFID chip of the test tube rack, wherein coupling of the RFID chips attached to the test tube racks is independent of the direction of insertion of the test tube rack.

17. A rack assembly for holding a plurality of laboratory racks for holding at least one laboratory vessel, comprising:
a plurality of rack receptacles capable of holding the laboratory racks in a row-and-column structure, the laboratory racks having a generally rectangular shape with a RFID chip applied to one side surface in a position offset as to the center axis of the laboratory rack, such that the location of the RFID chip determines the orientation of the laboratory rack and the position of the at least one laboratory vessel, and a plurality of antenna structure elements for wireless coupling with the RFID chip of the laboratory rack, wherein each antenna structure element comprises a substantially flat carrier substrate with a first carrier surface and a second carrier surface opposite the first carrier surface, and comprising at least two antennas applied on the carrier substrate, wherein a first antenna of the at least two antennas is applied on the first carrier surface and a second antenna of the at least two antennas is applied on the second carrier surface, the two antennas being applied on the two carrier surfaces in a staggered format such that the offset between the two antennas corresponds to two possible locations of the RFID laboratory rack chip to be read in the rack assembly, the at least two antennas positioned on alternating locations on the first and second carrier surfaces offset to each other by a distance corresponding to the position of the RFID chip of the laboratory rack, wherein coupling of the RFID chips attached to the laboratory racks is independent of the direction of insertion of the laboratory rack.

* * * * *